United States Patent [19]

Sneider

[11] Patent Number: 4,519,794
[45] Date of Patent: May 28, 1985

[54] VALVE CONTROL OF NOZZLE FLOW FROM DISPOSABLE SYRINGE

[76] Inventor: Vincent R. Sneider, 3422 Hallcrest Dr., Hampton Hall, Atlanta, Ga. 30319

[21] Appl. No.: 540,879

[22] Filed: Oct. 11, 1983

[51] Int. Cl.³ .............................................. A61M 1/00
[52] U.S. Cl. ................................... 604/212; 222/544; 604/279
[58] Field of Search ............... 604/212, 213, 275, 279, 604/39–42; 222/546, 548, 549, 554, 544

[56] References Cited

U.S. PATENT DOCUMENTS

| | | | |
|---|---|---|---|
| 3,118,578 | 1/1964 | Collins | 222/548 |
| 3,967,765 | 7/1976 | Micallef | 222/554 |
| 4,200,097 | 4/1980 | Hobbs, Jr. et al. | 604/213 |
| 4,351,336 | 9/1982 | Sneider | 604/212 |

Primary Examiner—John D. Yasko
Attorney, Agent, or Firm—Ralph R. Roberts

[57] ABSTRACT

This douche nozzle provides a linear valve which is constructed in the stem of the nozzle. This valve is closed to fluid flow when in the outer position and is open in the inner condition. The valve is made with telescoping tubular portions and a stop means is provided so that the linear valve is not accidently moved from its fluid flow stop condition and position. This nozzle is used with a collapsed flexible bag whose open end is fed through a tubular collar and the end of this bag is reversed with a short end portion brought along the outer surface of the collar. The nozzle has an enlarged end and a skirt portion which mates with and mounts on the outer portion of the collar so as to retain this bag with the nozzle.

20 Claims, 5 Drawing Figures

U.S. Patent  May 28, 1985  4,519,794
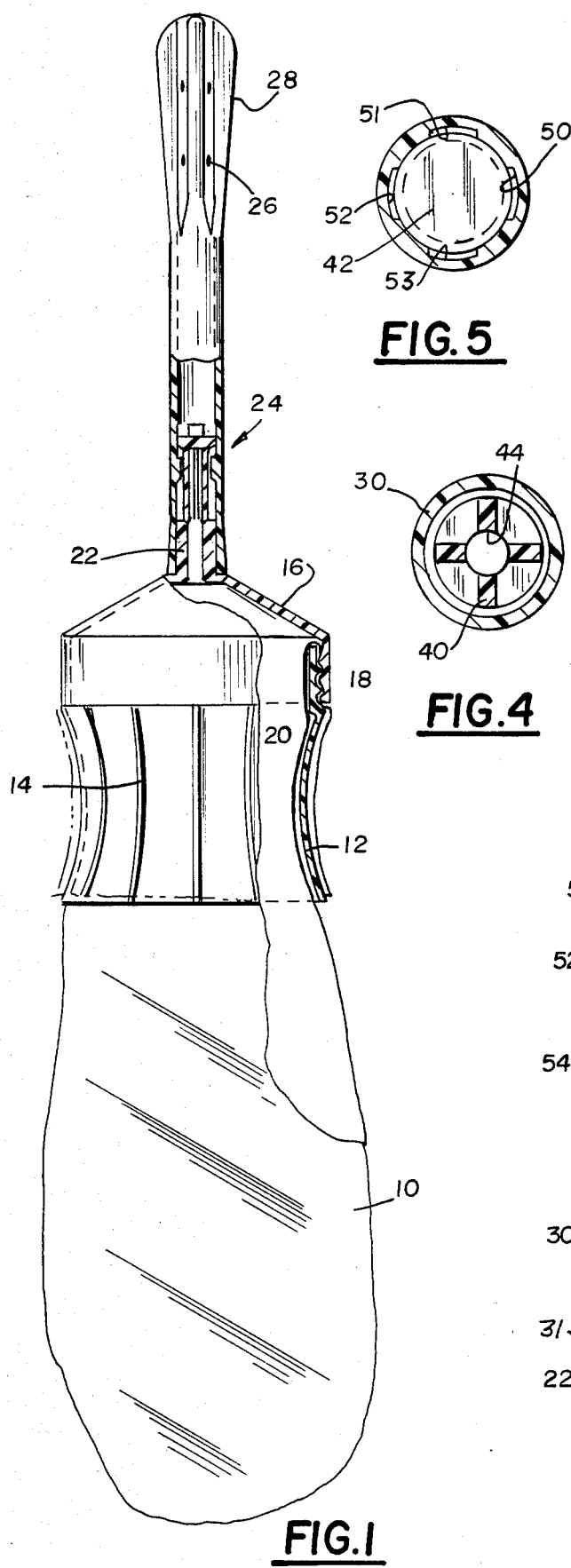
FIG.1
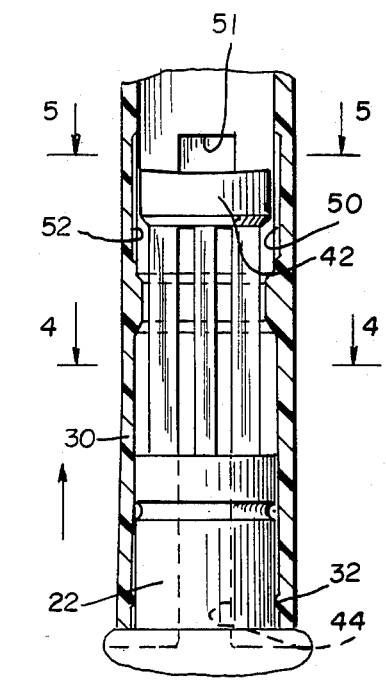
FIG.5
FIG.4
FIG.3
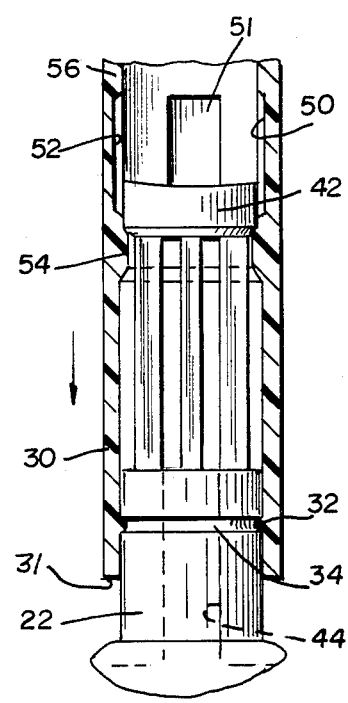
FIG.2

VALVE CONTROL OF NOZZLE FLOW FROM DISPOSABLE SYRINGE

CROSS REFERENCE TO PRIOR PATENT OF APPLICANT

To the extent applicable reference is made to the U.S. Pat. 4,066,080 as issued to the Applicant and pertaining to disposable syringes.

BACKGROUND OF THE INVENTION

1. Field of the Invention

This invention pertains to the field of art found generally in the Class entitled "Surgery" and particularly to the art in which flow control is provided for disposable vaginal douches.

2. Description of the Prior Art

Selectable valve control performed by a simple manipulation is well known. In particular are rotation of a stem portion as is found in oil and margarine containers and also in lighter fluid containers is well known. The valve control used in dispensers such as used in and by syrup dispensers and the like are also well known. These syrup containers and their slide valves are usually open when pulled outwardly and closed when at the inner limit.

Douch devices have often operated on the premise of reusability or of a kit which requires filling with liquid just prior to use. This invention contemplates such a douche device but the slide valve control portion is adapted to be closed when the stem control is at an outer limit and is open to fluid flow when the nozzle is pushed inwardly to near or at the inner limit of movement. This valve control has a small detent by which the slide valve is secured in the closed condition and accidental dislodgement is minimized.

In applicant's previous U.S. Pat. No. 4,066,080 at FIGS. 10, 11 and 12 a slide valve is depicted, but this slide valve has a key to prevent turning of the portions forming this valve and said valve is closed when in the inner position or condition. The slide valve of the present invention is provided in the stem portion of the nozzle.

SUMMARY OF THE INVENTION

This invention may be summarized, at least in part, with reference to its objects.

It is an object of this invention to provide, and it does provide, an improved douche nozzle that has a flow control valve that is closed with the stem portion extended outwardly and is open when the stem portion is pushed inwardly to the shank. This inward movement of the stem usually occurs as the entering nozzle end is manipulated into the body opening.

It is a further object of this invention to provide, and it does provide, a slide valve formed in and as a portion of the stem of a douche device and used with a douche device which contemplates a collapsible bag that is easily assembled to a retaining collar member and in a retained position is filled and then mounted to a nozzle. The stem of this nozzle has a valve formed in the stem portion. This valve is a slide valve that is closed when in the extended condition and is open when the stem is pushed to its inner condition. A detent means is provided so as to establish and maintain the valve in the closed condition.

In brief, this disposable douche is contemplated to be essentially of plastic. The collapsible bag used with this device is usually of thin flexible plastic. A medicament powder is usually provided in this bag. A collar member is provided and the open end of this bag is manipulated through this collar member and the end is positioned over the outer portion of said collar. This collar member usually is provided with male threads and an enlarged member of the nozzle is molded with compatable threads. The end and collar members are tightened in position with the open end of the collapsible bag retained therebetween. The nozzle of this douche is of a generally conventional configuration. The entering end of the nozzle is configured and contoured in a conventional manner.

The stem of the nozzle is made to include a molded valve that provides flow control of fluid in the bag. This valve is closed at its outward position and open when the stem is slid to an inner or shortened condition. A detent is provided in compatible stem portions so that the stem is retained in the flow inhibiting position except when it is desired to move the valve to a fluid flow condition. The stem portion is molded as a part of the collar end of the nozzle and is provided with a fluid bypass and a closed end which engages a reduced diameter portion in the nozzle stem portion to provide the seal. A bypass is formed in the nozzle stem portion of the entering end member.

BRIEF DESCRIPTION OF THE DRAWING

FIG. 1 represents a side view, partly diagrammatic and partly in section and showing the disposable douche of this invention assembled for use and with the nozzle valve in the open fluid flow condition;

FIG. 2 represents in an enlarged scale, partly fragmentary and partly diagrammatic and in section a side view of the slide valve in a fluid closed condition;

FIG. 3 represents the sectional side view of the slide valve of FIG. 2 but with the valve now moved to a fluid flowing condition;

FIG. 4 represents a sectional transverse view taken on the line 4—4 of FIG. 3 and looking in the direction of the arrows, and FIG. 5 represents a sectional transverse view taken on the line 5—5 of FIG. 3 and looking in the direction of the arrows.

In the following description and in the claims various details are identified by specific names for convenience. These names are intended to be generic in their application. Corresponding reference characters refer to like members throughout the several figures of the drawings.

EMBODIMENT OF FIGS. 1 THROUGH 5

Referring next to the drawing and in particular to the valve nozzle shown therein, it is to be noted that the nozzle is primarily for use with a disposable douch syringe. A thin collapsible bag 10 is usually shipped in a non-filled condition and water or like fluids are added at the point of use. A collar member 12 (tubular) is of wasp-shaped configuration and is usually of molded plastic. This collar member is usually provided with raised grip portions 14 adapted to assist turning when the hand or hands of the user are wet.

A end member 16 is formed of molded plastic and has female screw threads 18 which mate with male threads 20 formed on the collar 12. A stem portion 22 is formed on end 16 and slidable thereon is a nozzle end member generally identified as 24. The distal end of this nozzle is provided with a plurality of discharge apertures or holes 26 and a rounded or contoured end portion 28 which enables smooth or easy penetration to be made by the nozzle when this end is entered into a body opening.

In FIG. 2 the valve construction is depicted when this end is in an open condition. An outer sleeve-like stem portion 30 of the nozzle 24 is sized so as to be slidable on and along the stem 22 of end member 16. The stem portion 30 has a terminal end 31 and a short distance therefrom is a shallow inwardly extending ring 32 which engages and seats in a shallow groove 34 in stem 22. It is to be noted that the ring 32 may be a plurality of detents whose only purpose is to provide a positioning means whereby the nozzle 24 is not accidently dislodged from the outer position and retains the nozzle in the closed or "fluid-stop" condition. The stem portion 22 is also provided with ribs 40 and as shown in FIG. 4 are four in number. An end cap 42 is at the end of the stem 22 and closes passage 44. Passage 44 (FIG. 4) is in flow communication with the interior of the end member 16 and between rib portions 40.

Seen in FIGS. 2, 3, and 5 are longitudinal by-pass passages 50, 51, 52 and 53 which are shallow and are formed in the inner wall of outer stem 30. These passages are disposed between a circular ring-like portion 54 and the stem wall 56 as seen in FIGS. 2 and 3.

It is to be noted that the circular ring-like portion 54 formed interior of and as a portion of the wall of stem portion 30 is made with a bevel shoulder or edge that engages the cap portion 42 of stem portion 22. Mating bevels on members of the stem portions form sealing surfaces or means and also enable the slight resiliency of stem members to slide into position. It is also to be noted that the groove 34 and the ring or detents 32 are sufficiently shallow to enable deliberate movement of the valve assembly from the closed condition of FIG. 2 to the open or flow position of FIG. 3. Usually ring 32 is made as a full ring portion to engage the outside of stem 22 and provide a fluid seal during the movement from closed to open flow condition.

USE AND OPERATION

The disposable douche assembly of this invention contemplates that bag 10 be of a thin plastic which is substantially impervious to liquid. This bag is conventionally of tube material, closed or sealed at one end and transversely trimmed and open at the other. This bag is stored and shipped in a dry and flat condition and at time or use usually has a powder or granules thereifn which are mixed with tap water to provide the desired solution. This bag in a dry and collapsed condition has its open end manipulated through the bore of collar member 12 and is doubled over the outside female threaded portion 18. The bag is now filled with tap water to provide the desired amount. The assembled nozzle member 24 is now brought to and over the bag 10 and screwed onto the threads so that the male threads 20 are advanced as far as possible. The upper end of the collar member 12 engages the slope of end member 16 to retain the bag 10, collar 12 and member 16 in a fluid tight manner. The raised grip portion 14 may be used if needed to effect this assembly.

The nozzle end member 24 is assembled and is assumed to be in the fluid stopped condition of FIG. 2. This disposable douche is now brought to a body opening not shown. The entering end of the nozzle with apertures 26 and contoured end 28 is now used in the usual manner and with an inserting motion and with additional manipulation, if needed, is brought to the flow conditon of FIG. 3. Fluid from the bag 10 flows up or through passage 44 interior of the ribs 40. End cap 42 is now in way of or adjacent to passages 50, 51, 52 and 53 so that fluid flow continues to the discharge apertures 26 now within the body opening and in the body cavity. After the mixed fluid is discharged the douche assembly is usually discarded. If desired, a new bag 10 and powder may be supplied and the nozzle 24 and collar member 12 be reused with disassembly being easily achieved.

It is to be noted that ribs 40 are formed to be spaced inwardly from the interior surface of stem portion 30 of the outer telescoping member. The showing has the ribs of a lesser outer diameter than the ring-like portion 54. As seen in FIG. 4, the ribs 40 therebetween provide a large fluid passageway as well as passage 44. The by-passageways 50, 51, 52 and 53 provide fluid passage when the end cap 42 is brought along side or in alignment with them. It is also to be noted that groove 34 is shown as fomed in stem 22 and this size and position is made to accommodate ring 32. As shown, this arrangment is believed to be less expensive to mold than a reverse configuration. This is not to preclude forming a groove in the exterior tubular stem portion 30 and a ring on the stem 22. Other stop and positioning means may be provided if desired. What is necessary is that the positioned stop means inhibits accidental motion of the telescoping members and that the end cap 42 be sufficiently engaged with the circular ring-like portion 54 to effect a fluid seal.

It is also to be noted that the tubular stem portions 30 and the interior stem portion 22 be of a plastic which is easily molded and with reasonable size control of all operations. It is to be noted that the tubular end of stem portion 30 engages the end member 16 and it is contemplated that ring 32 provides the fluid seal during the fluid expelling through the apertures 26. In fluid closed condition of FIG. 2 it is noted that the inwardly extending ring-like portion 54 has a chamfer formed at the rib portion. This chamfer assists in assembly of the valve and the telescoping portions. As shown, FIGS. 2, 3, 4 and 5 are about three times normal size. Threads 18 and 20 are depicted but other securing means may be provided including bayonette locking.

The slide valve and its unique construction lends itself to a novel method for making, assembling and using the above identified slide valve, the essential steps include forming and providing a thin flexible bag of generally tubular configuration and using this bag for fluid storage. Another step includes forming and providing a tubular collar member having male threads formed on its outer surface and using this collar member for manipulating the bag through the inner passageway and with a small end portion reversed over the outer surface the bag is filled with a selected amount of fluid, usually tap water. A hollow nozzle is now provided and is molded of plastic and the stem portion is made with telescoping portions. Molding of this nozzle includes a smoothly contoured distal end having a plurality of discharge openings. This slide valve for flow control includes the further steps of forming the outer stem portion so as to be in side-by-side slidable relationship with an inner stem portion providing the inner member of the telescoping sections, said inner member formed so as to have an enlarged end member terminating with a skirt-like portion sized and adapted for mounting on and mating with the exterior surface of the collar member; forming the inner stem portion of the telescoping section with a fluid passageway and terminating said stem with a closed disk-like end cap and sizing said end cap so as to be slidable within the inner diameter of the hollow stem forming the exterior wall member, and forming this end cap so that the end or surface facing the enlarged end member is contoured and adapted to provide a fluid sealing surface; forming on the enlarged extending skirt portion of the inner stem member and the tubular collar with cooperating means for securing and retaining the end of the collapsed bag; forming and providing on the inner stem portion a plurality of longitudinal ribs so as to extend from said end cap to an inner stem portion adjacent the enlarged end portion, said ribs having their outer edges a determined distance in from the outer diameter of the inner stem; forming the outer wall portion of the telescoping stem portion with an inwardly extending ring-like portion which protrudes inwardly of the nominal inner diameter of this stem wall and forming this ring-like portion with a contoured end or edge adapted to engage the end cap and provide a fluid stop, this end or edge facing the distal end of the nozzle; forming in this outer wall portion and adjacent to said ring-like portion and toward the distal end of the nozzle a plurality of fluid passageways or bypasses, and forming cooperating stop means on the inner surface of the outer stem portion and on the outer surface of the inner stem portion, said stop means establishing and maintaining the fluid stop until deliberate movement of the sliding valve is achieved to overcome this stop means and move this valve to fluid flow.

Terms such as "left", "right", "up", "down", "bottom", "top", "front", "back", "in", "out" and the like are applicable to the embodiments shown and described in conjunction with the drawing. These terms are merely for the purposes of description and do not necessarily apply to the position in which the syringe nozzle with a slide valve for fluid control may be constructed or used.

While a particular embodiment of the syringe nozzle has been shown and described it is to be understood the invention is not limited thereto and protection is sought to the broadest extend the prior art allows.

What is claimed is:

1. A syringe nozzle attachable to a flexible bag for fluid storage and discharge, this nozzle having a fluid flow control slide valve provided in the stem portion of the nozzle, this syringe and slide valve flow control including:
   (a) a collapsible bag of thin flexible plastic and having a closed end and an open end;
   (b) a collar member of generally tubular configuration and having securing means provided at and on the outer surface thereof;
   (c) a hollow nozzle having a distal end adapted for insertion into a body opening, this distal end smoothly contoured and with discharge openings or apertures therein which are in flow communication with the interior of this hollow nozzle, and with this distal end of the nozzle becoming an integral hollow stem forming the exterior member portion of a telescoping section in which inner and outer members are sized so as to be slidable therealong;
   (d) a slide valve means provided in said telescoping section and with the outer hollow stem portion slidable over an inner stem portion extending from an enlarged end member, said enlarged end member terminating with a skirt portion sized and adapted to mount and mate with the exterior surface of the collar member, said skirt having means to engage and retain said nozzle on the collar member, said inner stem portion having a fluid passageway therein and terminating with a fixed diameter closed disc-like end cap which is sized so as to be slidable within the inner diameter of the hollow stem portion forming the exterior wall member of the telescoping portion of the stem, this end cap having that end or surface facing the enlarged end member and particularly the outer edge portion of said end cap contoured and adapted to provide a sealing edge or surface;
   (e) a plurality of longitudinal ribs extending from the end cap to said inner stem portion adjacent the enlarged end portion, these ribs interior of the outer telescoping stem portion and providing a fluid pathway from the interior passageway to the inner surface of the wall portion of the outer stem, this inner stem portion being tubular in structure and formed with a circumferential stop means provided intermediate the enlarged end member and said ribs;
   (f) an outer wall portion of the telescoping stem portions said outer wall an integral extension of the distal end of the nozzle and with this stem portion including a ring-like portion extending inwardly of the nominal inner diameter of the stem wall and with said ring-like portion having a contoured end or edge providing a fluid stop when in engagement with the end cap this stop facing toward the distal end of the nozzle and adjacent to said ring-like portion and in that inner surface toward the distal end there is formed a plurality of fluid passageways or by-passes, and
   (g) cooperating stop means formed on the inner surface on the outer stem portion of the telescoping section this stop means adapted to mate with and engage stop means formed on the outer surface of the extending stem portion of the inner member, said stop means establishing and maintaining a position of said valve so as to provide a fluid stop between the outer sealing edge of the end cap of the inner stem and the mating contoured edge of the ring-like portion of the outer telescoping portion,
   whereas the open end of said collapsible bag is manipulated through the collar member and then reversed over and down the outside of the collar for a short selected distance, at this condition fluid may be placed in the bag through the open end after which the terminating skirt portion of the nozzle is mounted to and on the collar member to secure and retain the bag after which the nozzle is positioned with its distal end in said body opening and then the slide valve is manipulated so the stop means is overcome and the telescoping sections are moved relative to each other to permit fluid to flow from the bag through the stem, past the ribs through the fluid by-passes in the outer telescoping portion and then to and through the discharge holes.

2. A syringe nozzle as in claim 1 in which the securing means for retaining the collapsible bag are male threads formed on the outer surface of the collar member and mating female threads formed on the skirt portion of the enlarged end member.

3. A syring nozzle as in claim 1 in which the bag is made of thin plastic film of tubular construction and with one end closed and the other end transversely cut to provide an easily manipulated end adapted for manipulating through the collar member and positioning said end alongside the outer surface of the collar member.

4. A syringe nozzle as in claim 1 in which all members of the nozzle, stem and collar ae made of semi-rigid and molded plastic.

5. A syringe nozzle as in claim 2 in which the collar member is made with a reduced waist configuration.

6. A syringe nozzle as in claim 5 in which the collar member is formed on its outer intermediate surface with a plurality of raised grips.

7. A syringe nozzle as in claim 1 in which the stop means is a shallow groove formed in the outer surface of the stem portion of the inner member and a mating shallow inwardly extending ring disposed near to the internal end of the outer stem member.

8. A syringe nozzle as in claim 1 in which the end cap of the inner stem portion is formed with a beveled surface at least on the face directed toward the enlarged end member, and a mating bevel is formed on the ring-like portion on the outer stem that extends inwardly from the inner wall.

9. A syringe nozzle as in claim 8 in which said ring-like portion is formed with a beveled surface at each edge.

10. A syringe nozzle as in claim 1 in which the ribs are formed so that their outer diameter is less than the inner diameter of the inwardly extending ring-like portion on the outer telescoping member and the fluid passageway is centrally disposed to produce a passageway interior of the ribs.

11. A method of making, assemblying and using a syringe nozzle attachable to a flexible thin plastic bag for fluid storage and discharge having a slide valve adapted for manipulating fluid flow and shut-off, the making of this slide valve and associated components including the steps of:
(a) forming and providing a collapsible bag of thin flexible plastic;
(b) forming and providing a tubular collar member having securing means formed on its outer surface;
(c) molding a hollow nozzle in which the distal end is adapted for insertion into a body opening, smoothly contouring said end and providing discharge openings which are in flow communication with the interior of said nozzle and with this hollow nozzle portion reduced in diameter and becoming an integral stem portion forming an exterior member portion of a telescoping section in which the sliding valve is constructed and with inner and outer member portions sized so as to be slidable therealong;
(d) forming the outer stem portion so as to be in side-by-side slidable relationship with an inner stem portion providing the inner member of the telescoping sections, said inner member formed so as to have an enlarged end member terminating with a skirt-like portion sized and adapted for mounting on and mating with the exterior surface of the collar member;
(e) forming the inner stem portion of the telescoping section with a fluid passageway and terminating said stem with a closed disk-like end cap and sizing said end cap so as to be slidable within the inner diameter of the hollow stem forming the exterior wall member, and forming this end cap so that the end or surface facing the enlarged end member is contoured and adapted to provide a fluid sealing surface;
(f) forming on the enlarged extending skirt portion of the inner stem member and the tubular collar cooperating means for securing and retaining the end of the collapsed bag;
(g) forming and providing a plurality of longitudinal ribs so as to extend from said end cap to an inner stem portion adjacent the enlarged end portion, said ribs having their outer edges a determined distance in from the outer diameter of the inner stem;
(h) forming the outer wall portion of the telescoping stem portion with an inwardly extending ring-like portion which protrudes inwardly of the nominal inner diameter of this stem wall and forming this ring-like portion with a contoured end or edge adapted to engage the end cap and provide a fluid stop, this end or edge facing the distal end of the nozzle;
(i) forming in this outer wall portion and adjacent to said ring-like portion and toward the distal end of the nozzle a plurality of fluid passageways or by-passes, and
(j) forming cooperating stop means on the inner surface of the outer stem portion and on the outer surface of the inner stem portion, said stop means establishing and maintaining the fluid stop until deliberate movement of the sliding valve is achieved to overcome this stop means and move this valve to fluid flow.

12. The method of making, assemblying and using a syringe nozzle as in claim 11 including providing the collapsible bag in a condition for transport and storage and absent fluid, said bag of thin plastic sheet material.

13. The method of making, assemblying and using a syringe nozzle as in claim 11 which includes the step of making the cooperating stop means as a shallow groove in one of the telescoping stem portions and a shallow ring in the other stem portion, said ring sized and positioned to engage said groove and establish the closed flow condition.

14. The method of making, assemblying and using a syringe nozzle as in claim 13 which includes forming said shallow groove in the stem portion of the inner member and intermediate the ribs and enlarged end member and forming the shallow ring inwardly of the inner diameter of the outer stem portion and positioning this shallow ring near a terminal end of said stem.

15. The method of making, assemblying and using a syringe nozzle as in claim 11 which further includes forming the disk-like end cap with a chamber disposed toward the enlarged end member and forming the ring-like portion of the outer wall portion with a mating chamfer adapted to provide the fluid stop surface.

16. The method of making, assemblying and using a syringe nozzle as in claim 15 which further includes forming the ring-like portion of the outer wall with an outwardly directed chamber on its opposite end, said outwardly directed chamber providing a guide means for advancing the closed disk-like end cap thereby.

17. The method of making, assemblying and using a syringe nozzle as in claim 11 which includes forming the plurality of ribs with their outer diameter or extent less than the inner diamteter of the ring-like portion of the outer wall.

18. The method of making, assemblying and using a syringe nozzle as in claim 11 which includes forming male threads on the exterior surface of the collar member to provide one portion of the cooperating retaining means and forming mating female threads on the inner surface of the skirt-like portion of the enlarged end member to provide the other retaining means, said male and female threads formed so as to have sufficient clearance for retaining the end of the collapsible bag.

19. The method of making, assemblying and using a syringe nozzle as in claim 18 which includes forming the collar member with a concave or wasp-like configuration.

20. The method of making, assemblying and using a syringe nozzle as in claim 19 which further includes forming a plurality of gripping ribs which extend outwardly from the outer surface of the collar member and with the male threads on said collar member formed at an end of said collar member.

* * * * *